United States Patent
Schlangen et al.

(10) Patent No.: US 9,820,365 B2
(45) Date of Patent: Nov. 14, 2017

(54) LIGHTING SYSTEM WITH A DAILY RHYTHM AND DIM LIGHT DYNAMICS

(71) Applicant: PHILIPS LIGHTING HOLDING B.V., Eindhoven (NL)

(72) Inventors: Lucas Josef Maria Schlangen, Eindhoven (NL); Gabrielle Johanna Bernarda Maria Meekes, Geldrop (NL); Johannes Petrus Wilhelmus Baaijens, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 15/021,985

(22) PCT Filed: Sep. 17, 2014

(86) PCT No.: PCT/EP2014/069744
§ 371 (c)(1),
(2) Date: Mar. 15, 2016

(87) PCT Pub. No.: WO2015/040036
PCT Pub. Date: Mar. 26, 2015

(65) Prior Publication Data
US 2016/0234911 A1    Aug. 11, 2016

(30) Foreign Application Priority Data
Sep. 23, 2013   (EP) ..................................... 13185513

(51) Int. Cl.
*H05B 37/02*   (2006.01)
(52) U.S. Cl.
CPC .................................. *H05B 37/029* (2013.01)

(58) Field of Classification Search
CPC ...... H05B 37/02; H05B 37/029; H05B 33/08; H05B 33/0812; H05B 33/0818; H05B 33/0824
(Continued)

(56) References Cited

U.S. PATENT DOCUMENTS 5,589,741 A * 12/1996 Terman .............. H05B 37/0218
315/156
8,952,626 B2 * 2/2015 Huang ................. H05B 37/029
315/158

(Continued)

FOREIGN PATENT DOCUMENTS

EP            2635093 A2    9/2013
JP        2000294387 A    10/2000
(Continued)

*Primary Examiner* — Jimmy Vu

(57) ABSTRACT

The invention provides a lighting system (100) comprising a first lighting element (10) and a control unit (50), wherein: a) the first lighting element (10) is configured to provide first lighting element light (11) with controllable lighting intensity, wherein the first lighting intensity can be selected from a plurality of values in the range of 0-I, with I being a predetermined first lighting element maximum intensity; b) the control unit (50) is configured to maintain a first lighting element intensity, during a first predetermined period at an intensity value larger than zero when a general lighting intensity is below a predetermined first threshold level; c) the control unit (50) is further configured to maintain the first lighting element intensity during a second predetermined period at an intensity value a*y*I when the general lighting intensity level is y*I, y being the factor the general lighting intensity is below I, with 0<y<1, the parameter a being a predetermined lighting setting with 0<a≤1/y; and d) the lighting system is further configured to provide during a third predetermined period first lighting element light (11) with a dynamic property selected from the group of a (Continued)

moving or changing light pattern, a color change, and an intensity change.

13 Claims, 3 Drawing Sheets

(58) Field of Classification Search
USPC ... 315/209 R, 291, 307, 308, 153, 156, 159, 315/360; 362/249.02, 249.06
See application file for complete search history.

(56) References Cited

U.S. PATENT DOCUMENTS

| | | |
|---|---|---|
| 2003/0231495 A1 | 12/2003 | Searfoss |
| 2004/0012487 A1* | 1/2004 | Burns .................. G08B 5/36 340/332 |
| 2014/0312780 A1* | 10/2014 | Vissenberg .......... G01B 11/026 315/153 |

FOREIGN PATENT DOCUMENTS

| | | |
|---|---|---|
| WO | 2007114614 A1 | 10/2007 |
| WO | 2010079388 A1 | 7/2010 |
| WO | 2012011008 A1 | 1/2012 |
| WO | 2012095765 A2 | 7/2012 |

* cited by examiner

LIGHTING SYSTEM WITH A DAILY RHYTHM AND DIM LIGHT DYNAMICS

CROSS-REFERENCE TO PRIOR APPLICATIONS

This application is the U.S. National Phase application under 35 U.S.C. §371 of International Application No. PCT/EP2014/069744, filed on Sep. 17, 2014, which claims the benefit of European Patent Application No. 13185513.2, filed on Sep. 23, 2013. These applications are hereby incorporated by reference herein.

FIELD OF THE INVENTION

The invention relates to a lighting system and a method for controlling lighting in a room, for instance with such lighting system. The invention also relates to a computer program product, when run a computer, being configured to control a lighting system according to such method.

BACKGROUND OF THE INVENTION

The generation of light cycles is known in the art. U.S. Pat. No. 5,589,741, for instance, describes a naturalistic illumination system for a user at a location having a light source for providing illumination of variable intensity above a non-zero value to the user location. A computer produces a variable signal to control a cycle of variable intensity illumination level output of the light source to correspond to the progressive variation in light level intensity above a non-zero value over a selected time of day period at a geographical location as selected from a computer input device. The variable signal is produced on a daily basis to produce the variable intensity illumination cycle for the same period of time in a manner to progressively shift the time of the start of the production of the variable intensity illumination cycle for the period of time each day over a period of successive days relative to the normal time of start of the production of the variable intensity illumination cycle during the period of successive days at the selected geographical location. The variable signal also can be produced to shift the time of start of the variable intensity illumination cycle for each day and to cause a dawn to dusk or dusk to dawn transition of the illumination cycle transition.

SUMMARY OF THE INVENTION

Light coming in the eye and falling upon a third photoreceptor regulates the biological clock in mammals. The biological clock has a daily rhythm which can be influenced by light. The biological clock regulates our sleep-wake rhythm and impacts well-being. Moreover, dynamic light effects can play an important role in the well-being and sleep-wake regulation of people. The room ambience impacts the stress levels and affective state of the person living in that room. This can have a positive influence on the sleep-wake cycle, when a person becomes less stressed and more relaxed in a pleasant atmosphere while falling asleep or returning to sleep after a nocturnal awakening. Dynamics light effects can be used to activate or unwind people on different moments of the day.

The sleep-inducing nocturnal 'hormone of darkness' melatonin is often used as a marker for the biological clock and the sleep-wake rhythm of an individual. Consolidated sleep is only possible during melatonin secretion. Light at night is known to enhance alertness but also suppresses the melatonin secretion, compromising sleep. Melatonin is known to have radical scavenging properties and seems to be involved in protection against tumorgenesis and tumor growth, another reason why melatonin suppression is not desired. For optimal sleep, (near) darkness is the most favorable condition to sleep in.

Darkness or dim light can make people (like demented elderly, babies and children) feel uncomfortable, and does not always provide the right ambience to unwind and relax while falling asleep, or when trying to return to sleep. Darkness or dim light conditions are needed for good and consolidated sleep, but do not always provide an attractive atmosphere/ambience to fall asleep, or quickly return to sleep after nocturnal awakenings. In many care environments like elderly care-homes pediatric wards, geriatric wards or NICU (neonatal intensive care units) facilities, the sleep of the individuals cared for is not optimal. The current general lighting systems in care institutions do not allow for light settings that promote a rapid sleep onset.

Hence, it is an aspect of the invention to provide an alternative lighting system and/or an alternative lighting method (or method for controlling lighting in a room), which preferably further at least partly obviate one or more of above-described drawbacks. It is further an aspect of the invention to provide an alternative computer program product that may be used to execute the method (when run on a computer).

It surprisingly appears that the use of dynamic (dim) light effects may help creating a more pleasant atmosphere that facilitates a rapid sleep onset, or a rapid return to sleep after a nocturnal awakening. However, dynamic dim light effects are never provided within general lighting systems in e.g. hospital patient rooms, neonatal intensive care units, elderly care facilities or hotel-/bed-rooms.

Hence, in a first aspect the invention provides a lighting system ("system") comprising a first lighting element (herein also indicated as "night light" or "dim light") and a control unit, wherein a) the first lighting element is configured to provide first lighting element light with controllable (lighting element) intensity, especially controllable (lighting element) luminous flux, wherein the lighting element luminous flux can especially be selected from a plurality of values in the range of 0-$\Phi$, with $\Phi$ being a predetermined first lighting element maximum luminous flux (functionality a);

b) the control unit is especially configured to maintain a first lighting element illuminance at a first position (p1) within a first distance (d1) from the lighting element, with the first distance especially selected from the range of 0<$d1$≤15 m (see also below), during a first predetermined period at a specific (variable) intensity, especially at an illuminance value larger than zero, when a general lighting illuminance level at said first position (p1) is below a predetermined first threshold level (functionality b);

c) the control unit is further especially configured to maintain the first lighting element illuminance at said first position (p1) during a second predetermined period at an illuminance value a*y*E when the general lighting illuminance level at said first position (p1) is y*E, y being the factor the general lighting illuminance is below E, with 0<$y$≤1, parameter a being a predetermined lighting setting with 0<$a$≤1/y, and with E being the predetermined first lighting element maximum illuminance at said first position (p1) (functionality c); and d) the lighting system is further especially configured to provide during a third predetermined period first lighting element light with a dynamic property, especially selected from the group of a moving or a changing of a light pattern, a color change, and an intensity change, wherein especially during the third period a plurality of times one or more of the following sequentially takes place (i) the moving of the light pattern, (ii) the changing of the light pattern), (iii) the color change of the first lighting element light, and (iv) the intensity change of the first lighting element light (functionality d).

In yet a (more general) aspect the invention provides a lighting system comprising a first lighting element and a control unit for controlling the first lighting element to provide a first lighting element light, wherein the lighting system is configured to (a) adapt during a (first) predetermined period the first lighting element light to a general lighting level, and (b) provide during a further predetermined period the first lighting element light further comprises a dynamic property selected from the group of moving or changing a light pattern, changing a color, and changing an intensity of said first lighting element light. Especially, such lighting system may be configured to (b) adapt during a second predetermined period the first lighting element light to a dimmed lighting level wherein the dimmed lighting level further comprises a dynamic property selected from the group of moving or changing a light pattern, changing a color, and changing an intensity of said first lighting element light. The (first) predetermined period and the further (or second) predetermined period may in an embodiment be two different periods or may in another embodiment be partially or entirely overlapping periods. For instance, in the former embodiment first first lighting light may be provided of which the intensity may be adapted to a general lighting level and during a second period, the dynamic lighting may be provided, of which the intensity may optionally especially (also) be adapted to a general lighting level. Hence, in this way for instance dimmed light with a dynamic effect may be provided. For instance, the (first) predetermined period may be a period during the day, and the further predetermined period may be a nocturnal period. Further, especially during said further (or second) period a plurality of times one or more of the following sequentially may take place (i) the moving of the light pattern, (ii) the changing of the light pattern), (iii) the color change of the first lighting element light, and (iv) the intensity change of the first lighting element light. Especially, the dynamic property includes one or more of a color change and a light pattern change.

With such lighting system(s), it is possible to provide light ("first lighting element light") during periods of sleep, or during a period a person may desire to fall asleep or should fall asleep, or during a period a person desires to wake up or should awake, which may fit well to the specific period. The lighting system may adapt the light intensity of the first lighting element (and optionally other lighting elements when available in the lighting system) to a general lighting (intensity level) that is available, and even to the varying intensity (level) of such general lighting. Further, the lighting system may provide dynamics in the lighting (i.e. first lighting element light) which may not be too fast and which may not be too slow, especially during the period a person may desire to fall asleep or should fall asleep and/or during a period a person desires to sleep or should sleep. Hence, also during a nocturnal awaking such dynamic lighting may be provided, which may assist in falling asleep again.

The lighting system may use dynamic dim light during part of its, preferably 24 hr., rhythm. The dynamic dim light effects yields specific emotional and/or health and well-being benefits. They shape an ambience (for instance a starry sky) in a patient (bed) room or elderly (bed) room or baby (bed) room that makes the person in the bed more relaxed and less stressed, thus having a positive influence on the time it takes to fall asleep. The dynamics and spectral composition (such as blue deprived), and (low) intensity of the dim light condition is chosen not to suppress nocturnal melatonin secretion.

This invention may especially include a method (see also below) for the controlled lighting of an area by means of a lighting system. For instance, the method may comprise a predetermined time program that provides (1) general lighting during a predetermined general lighting period, (2) dynamic dim light effects (with first lighting element light) during a dim light period where the luminance or illuminance levels are low while some of the (il)luminated areas are dynamic in their location, intensity and/or spectral composition, with the dynamic cycle time being in the interval of especially 1 second-6 hours, especially 1 second to 3 hours, even more especially 1 second to 30 minutes, like 1-420 seconds, such as especially 1-120 seconds, such as at least 10 seconds, like at least 5 minutes.

Especially, the entire time program may run for more than 6 hrs., preferably 24 hrs., or especially a plurality of days (of 24 hours). Such entire program may address the herein indicated predetermined periods, like especially the first, second and third periods.

Further, the method (and lighting system) may include a control unit configured to control the lighting system according to the predetermined time program. Further, especially the dynamic light effects (of the first lighting element light) are either created via projection of moving images or with patterns of light dots on a pixelated light exit window, such as in a specific embodiment a ceiling luminaire. Optionally, more than one kind of nocturnal dynamic dim light light effect can be envisioned for different purposes/times, especially one or more of (a) falling asleep, (b) nocturnal awakenings, and (c) waking up. Alternatively or additionally, the system can be connected to bio feedback signals. Further, also alternatively or additionally in embodiments the user can personalize the dynamic light effects via a user interface. Hence, amongst others the invention may include a lighting system with a daily rhythm that includes a period with special dim (and/or bright) light dynamics, amongst others dedicated to fall asleep (and/or wake-up) more easily.

As indicated above, the lighting system at least comprises a first lighting element. The lighting element comprises one or more light sources that provide light. Further, the first lighting element comprises a light exit window. A user may perceive light from the first lighting element escaping from such light exit window. Hence, the first lighting element light is especially light downstream from the light exit window. This light may for instance be perceived directly, or indirectly. For instance, with respect to the latter embodiment, the first lighting element may be configured to project (during the third period) a light pattern on a ceiling.

The terms "upstream" and "downstream" relate to an arrangement of items or features relative to the propagation of the light from a light generating means (here the especially the first lighting element), wherein relative to a first position within a beam of light from the light generating means, a second position in the beam of light closer to the light generating means is "upstream", and a third position within the beam of light further away from the light generating means is "downstream". The term "first position" may also refer to a plurality of first positions, such as e.g. at a ceiling and at a wall. Hence, dynamic effects may for instance be displayed at two or more positions in a room.

Optionally, the properties of the first lighting element light (as described herein) at two or more first positions may be independently controllable. For instance, the dynamic effects may differ from first position to other first position.

Especially, the first lighting element comprises the ability to tune the intensity of the first lighting element light. Not only off (zero intensity) and maximum intensity (indicated with "E", see also below), but also values in between can be chosen. Hence, a plurality of intensities can be chosen, such as in addition to zero intensity and maximum intensity, also at least 4, even more especially at least 10 different intensities. Hence, the first lighting element has a controllable light intensity. The control unit is configured to control this intensity. Especially, the first lighting element has a maximum luminous flux of 10,000 lumens, even more especially a maximum luminous flux of 5,000 lumens. Further, the lighting element illuminance can (thus) be selected from a plurality of values in the range of 0-Φ, with Φ being a predetermined maximum first lighting element illuminance. The controllable intensity is herein also indicated as functionality a).

Further, the control unit may especially be configured to maintain the first lighting element illuminance at a first position (p1) within a first distance (d1) from the lighting element, with the first distance especially selected from the range of 0<d1≤15 m. The lighting element may be designed in such a way that the illuminance at 1 meter (d1=1 m) is at maximum 50 lux. This may for instance be of interest for application on a night stand or pedestal cupboard. The luminous flux is the total amount of light from a light source defined towards the sensitivity curve of the human eye. Luminous flux has as unit Lumen (Lm). The illuminance is the luminous flux that hits an area divided by the size of the area. The illuminance is indicated with Lux (lx) and can be defined as Φ/A. The illuminance may thus decrease with increasing distance from the source of light. The luminous flux or illuminance of the first lighting element are thus especially due to the first lighting element light generated by said first lighting element (during use).

One may also consider other applications, like over a bed or in a room with multiple beds. In such applications the illuminances may be chosen differently, such as e.g. smaller and larger than 50 lux, respectively.

In general however, the illuminance at (first position p1, to be chosen to be) 1 meter from the first lighting element will not be larger than 50 lux. The maximum first lighting element illuminance (or luminous flux, see also below) may be due to the physical maximum intensity the lighting element can provide. It may however in other embodiments also be a value that is controlled by the control unit. Such value may be preset (see also below). However, alternatively or additionally, a sensor may be applied. Such sensor and control unit may then be configured to evaluate the illuminance at said first position. This might include a direct measurement or estimation. Especially, the first position may be a bed or part of a bed in a room. Hence, the maximum illuminance (or luminous flux) may be defined dependent upon the specific application. Hence, especially 0.5≤d2≤5 m. In an embodiment, the first lighting element may (be configured to) have a maxium illuminance at the first position (p1) within a first distance (d1) from the lighting element, with the first distance 0<d1≤15 m, especially 0.5≤d2≤5 m, in the range of 20-100 lux, especially in the range of 40-60 lux, such as 50 lux.

The first lighting element may comprise a single light source or a plurality of light sources. Especially, the first lighting element comprises one or more LED light sources.

In a specific embodiment, the light source comprises a solid state LED light source (such as a LED or laser diode). The term "light source" may also relate to a plurality of light sources, such as 2-20 (solid state) LED light sources. Hence, the term LED may also refer to a plurality of LEDs. However, also more LEDs may be applied in the first lighting element. Further, the term "first lighting element" may also refer to a plurality of first light elements. The total luminous flux provided by such plurality of first lighting elements will be, as indicated above, especially be equal to or lower than 10,000 Lumen, more especially equal to or lower than 5,000 Lumen. Likewise, the total illuminance at position p1 due to the first lighting element may especially be equal to or lower than 100 lux, especially equal to or lower than 50 lux (at position p1).

Especially, the first lighting element provides lighting element light that is blue deprived, i.e. for instance white light that has a color temperature below 4000 K or light that is non-white due to a deficit of blue light, especially due to a complete lack of blue light in the spectrum emitted by the element. The use of colored light may help to reduce a certain undesired biological response (like alerting people at night).

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL.

The terms "violet light" or "violet emission" especially relates to light having a wavelength in the range of about 380-440 nm. The terms "blue light" or "blue emission" especially relates to light having a wavelength in the range of about 440-490 nm (including some violet and cyan hues). The terms "green light" or "green emission" especially relate to light having a wavelength in the range of about 490-560 nm. The terms "yellow light" or "yellow emission" especially relate to light having a wavelength in the range of about 540-570 nm. The terms "orange light" or "orange emission" especially relate to light having a wavelength in the range of about 570-600. The terms "red light" or "red emission" especially relate to light having a wavelength in the range of about 600-750 nm. The term "pink light" or "pink emission" refers to light having a blue and a red component. The terms "visible", "visible light" or "visible emission" refer to light having a wavelength in the range of about 380-750 nm.

The lighting element may further comprise the functionality to provide dynamic properties to the light of the first lighting element. This will further be elucidated below.

The first lighting element may comprise a plurality of functionalities.

In embodiments, the control unit is especially configured to maintain the first lighting element illuminance at said first position (p1) during a first predetermined period at a specific (variable) intensity, especially at an illuminance value larger than zero, when a general lighting illuminance level at said first position (p1) is below a predetermined first threshold level.

This functionality (b) may assure that when the general lighting level is below a specific value (including zero), the first lighting element provides light. This can also be considered a "night light" or "dim light" functionality.

In a specific embodiment, the predetermined first threshold level (at the same first position) of the general lighting illuminance is 100 lux or smaller, especially 50 lux or smaller, or even 10 lux or less, such as 5 lux or less. If larger than 50 lux, the lighting system may be used in rooms wherein it may be relatively light, such as during the day. A threshold of 50 lux or lower may especially relevant during the night. The predetermined first threshold level may be larger than zero, but its value may in embodiments be defined dependent upon the intended application. Alternatively, in an embodiment the threshold is defined as a luminous flux threshold (of all other (artificial) light sources than the first lighting element) of 5,000 lumen or smaller, especially 500 lumen or smaller, or even 100 lumen (or lower), as also indicated below. Note that the predetermined first lighting element maximimum luminous flux is especially 10,000 Lumen, even more especially 5,000 Lumen. In further embodiments, the predetermined first lighting element maximimum luminous flux may even be lower, such as 500 Lumen, like 100 Lumen.

This general illuminance level may refer in embodiments to an illuminance provided by one or more other lighting elements which are also part of the system. In such embodiments, the control unit can control the lighting intensity of the first lighting element as function of the general illuminance level of the one or more other lighting elements. These one or more other lighting elements, when being functionally included in the lighting system, are herein also indicated as "second lighting element". Based one or more of a (light) sensor, a time program, etc., the control unit can evaluate the status of the second lighting element, and based thereon control the first lighting element. Note that when such general lighting is switched off, the general lighting illuminance will be zero by (this) definition (as general illuminance level may refer in embodiments to illuminance provided by one or more other lighting elements which are also part of the system).

Hence, in a specific embodiment, the lighting system further comprises a second lighting element configured to provide second lighting element light; the general lighting illuminance may especially be defined as the illuminance at said first position (p1) provided by said second lighting element light.

In yet a further embodiment the luminance in the room resulting from the first lighting element has a maximum value of 50 cd/m$^2$ and the second lighting element achieves a maximum luminance value of 20,000 cd/m$^2$ within the room/space where the system is used.

In yet a further embodiment, the ratio of the maximum luminance of the first lighting element and the second lighting element is at least 1:10, such as at least 1:50, like at least 1:100. Further, the first lighting element may also result in a (non-zero) minimum luminance (within the illuminated area) of at least 2 cd/m$^2$, especially a (non-zero) minimum luminous flux of at least 0.2 cd/m$^2$. Further, also the second lighting element may also have a (non-zero) minimum luminance (within all illuminated areas), especially of at least 20 cd/m$^2$, especially a (non-zero) minimum luminous flux of at least 20 cd/m$^2$. When the (second) lighting element comprises a plurality of (second) lighting elements, the cumulated (maximum) luminous fluxes should especially comply with (one or more of) above definition(s). Likewise, when the (second) lighting element comprises a plurality of (second) lighting elements, the cumulated (maximum) illuminances should especially comply with (one or more of) above definition(s). Alternatively or additionally, in yet a further embodiment, the ratio of the maximum luminous fluxes of the first lighting element and the second lighting element is at least 1:10, such as at least 1:50, like at least 1:100. In case of 5,000 lumen maximum luminous flux for the first lighting element and 100,000 lumen maximum luminous flux for the second lighting element, the ratio is 1:20.

The luminous flux or illuminance of the second lighting element are thus especially due to the second lighting element light generated by said second lighting element (during use).

The maximum luminous flux (or other maximum intensities) may be defined by the specifications of the lighting element and optionally also by the control unit. Likewise, the maximum illuminance is defined by the specifications of the lighting element and optionally also by the control unit. For instance, optionally the first lighting element may provide enough intensity to provide an illuminance >100 lux (at the first position (p1)). However, the control unit may define the predetermined first lighting element maximum illuminance to be 50 lux (see also above).

Further, in general the illuminance at 1 meter from the first lighting element is at least 0.5 lux, especially at least 1 lux, especially during one or more of the herein described first predetermined period, second period and third period. This lower (non-zero) level may be based on the lighting element specifications, but may also be controlled by the control unit.

In a yet another specific embodiment, the general lighting illuminance is defined as the illuminance at said first position (p1) provided by light of any lighting element except for said first lighting element light. Especially then, the lighting system may further comprises a first sensor, wherein the control unit and said first sensor are configured to evaluate the general lighting illuminance at said first position (p1). In such embodiment, natural light may be included in the general lighting illuminance, or when no other lighting elements are available except for the first lighting element, only natural light may be included in the general lighting illuminance. As now the general lighting illuminance may include contribution of sources that are not part of the lighting system, such as daylight or light from the moon, etc., the lighting system may especially also include such first sensor. The term "sensor" may also relate to a plurality of sensors.

Note that the illuminance of the first lighting element is not considered to contribute to the general lighting illuminance and that light of any other light source when part of the system and/or from other light sources may be considered general lighting (see definitions above).

The (first) predetermined period can be a period that returns each day, and may be triggered by a time clock or digital time schedule, or by light conditions that are sensed by a sensor, such as above indicated first sensor. The first predetermined period can be triggered by a manual trigger. Hence, the control unit may include a (remote) user interface functionally coupled to said control unit. The first predetermined period may thus embodiments be a fixed period, such as 8 hours from 10 pm to 6 am, but may optionally also be a period that defined by a user. The first predetermined period may be the time between sunset and sunrise but the first predetermined period may also be the period that e.g. the general lighting illuminance level is below 50 lux (or another threshold value) (see also below). In an embodiment, the functionality under b) is a default setting and the predetermined period is (thus) 24 hours. This may imply that always when the general lighting illuminance level is below the first threshold level, such as switched off, the first lighting element is switched on.

Anyhow, during said (first) predetermined period, the first lighting element may at least be switched on when the following applies: (1a) a second lighting element is comprised by the lighting system and said second lighting element is switched off, (1b) a second lighting element is comprised by the lighting system and said second lighting element provides second lighting element light (at said first position) below the threshold level, (2a) there is no further lighting element and the general lighting level (at said first position) is below the threshold level, (2b) a second lighting element is comprised by the lighting system and said second lighting element together with other light sources (like daylight) provide light (at said first position) below the threshold level. These options correspond to the above given definitions of general lighting illuminance.

Especially, the first lighting element is configured to provide at least 1 lux at the first position (during one or more of said first, second and third periods). In dark rooms, this may already be enough to be perceived by a user. Hence, the b) part especially provides a night light functionality.

In case the general lighting illuminance is non-zero, one may in embodiments chose the level of illuminance of the first lighting element. For instance, one may relate the illuminance of the first lighting element to the general illuminance level. Hence, the control unit may further especially be configured to maintain the first lighting element illuminance at said first position (p1) during a second predetermined period at an illuminance value $a*y*E$ when the general lighting illuminance level at said first position (p1) is $y*E$, y being the factor the general lighting illuminance is below E, with $0<y<1$, and parameter a being a predetermined lighting setting with $0<a\leq 1/y$. This parameter a can in embodiments be fixed, can be user selected, can be time dependent, etc.

Parameter a or (light) setting a may be fixed value or may be variable value. In embodiments it may also be that during a specific time parameter a is fixed and during a period parameter a is variable. Especially when the general lighting illuminance drops, the first lighting element (and optionally also the second lighting element when being part of the lighting system and (also) having a controllable light intensity) may be used to gradually decrease the overall illuminance and thereby prevent or reduce illuminance jumps.

Especially, the first lighting element may be used to gradually change the overall illuminance (or luminous flux or luminance) during the period a person may desire to fall asleep or should fall asleep to a level that may be comfortable during sleep. Further, especially the first lighting element may be used to gradually change the overall illuminance (or luminous flux or luminance) during the period a person may desire to wake up or should fall wake up to a level that may be comfortable during a wake up period.

The control unit is especially configured to control the first lighting element, even more especially its first lighting element light. Optionally, the control unit is further especially configured to control the second lighting element (when available), even more especially its second lighting element light. Hence, the control unit may in embodiments (e.g.) be configured to gradually decrease the first lighting element illuminance (or luminous flux, or luminance) from a first value to a second value. This may thus also imply that a gradually changes with time. The functionality that the first lighting unit in embodiments may be configured to gradually decrease the first lighting element illuminance (or luminous flux or luminance) from a first value to a second value may optionally be independent whether there (still) is a non-zero general lighting illuminance (or luminous flux or luminance) or whether the latter is zero, such as when e.g. the second lighting element would be switched off (and/or when all other light sources would be off or shielded off (with e.g. blindings)). Hence, when the control unit would be able to perceive that the general illuminance (or luminous flux or luminance) suddenly drops to zero, or would the control unit be able to product a zero general illuminance, then the control unit may further be configured to control the first lighting unit to provide a first lighting unit illuminance (or luminous flux or luminance) that matches as good as possible, together with the present general illuminance (or luminous flux or luminance), a previous general illuminance (or luminous flux or luminance) level. The control unit may thus be configured to delay changes in the general illuminance (or luminous flux or luminance) level and arrive with a delay at a desired illuminance (or luminous flux or luminance) level of the first lighting element. For instance, assume that the general lighting illuminance level is 200 lux or 50 lux, and assume that the predetermined maximum first lighting element illuminance (E) is 50 lux, and assume that the general lighting illuminance level drops suddenly to 10 lux, the control unit may control the first lighting illuminance level to 50 or 40 lux, respectively, to match as good as possible the general illuminance during the previous state. Subsequently, the control unit may gradually lower the illuminance of the first lighting element to a level of e.g. 20 lux. Then a user may still perceive the first lighting element and discriminate it from the general lighting illuminance. In these examples, E=50 lux, y=0.2, and a is first 5 and 4, respectively, and after a while the parameter a is 2. As the first lighting element cannot give more illuminance than its maximum E, parameter a is related to y.

In yet a further embodiment, the control unit is configured to control the predetermined lighting setting a to a value n, when $y\leq 1/n$, with n=2. In such embodiments, the first lighting element, such as a night light, provides light at least twice the background (assuming that this is feasible for the first lighting element, such as a night light).

Note that when a second lighting element is included in the system, the control unit may in embodiments be configured to gradually decrease the first lighting element illuminance (or luminous flux or luminance) and the second lighting element illuminance (or luminous flux or luminance) from a first value to a second value. In this way, even better a gradual decrease may be obtained. Hence, when for instance during a nocturnal period a user switches off or on the light, the lighting system may prevent a sudden jump in illuminance (or luminous flux or luminance) and provide a gradual decrease or increase.

The second predetermined period can be a period that returns each day, and may be triggered by a time clock or digital time schedule, or by light conditions that are sensed by a sensor, such as above indicated second sensor. The second predetermined period can be triggered by a manual trigger. Hence, the control unit may include a (remote) user interface functionally coupled to said control unit. The second predetermined period may thus embodiments be a fixed period, such as 8 hours from 10 pm to 6 am, but may optionally also be a period that defined by a user. The second predetermined period may be the time between sunset and sunrise but the second predetermined period may also be the period that e.g. the general lighting illuminance level is below 50 lux (or another threshold value). In an embodiment, the functionality under c) is a default setting and the predetermined period is (thus) 24 hours. This may imply that always when the general lighting illuminance level is below the first threshold level, the first lighting element is switched on.

In embodiments, the first predetermined period and second predetermined period may be defined as a single predetermined period. The phrase "adapt during a predetermined period the first lighting element light to a general lighting level" and similar phrases may especially refer to the above described first predetermined period and the second predetermined period.

As indicated above, in an embodiment the lighting system may further especially be configured to provide during a third predetermined period first lighting element light with a dynamic property, especially selected from the group of a moving or changing light pattern, a color change, and an intensity change. This dynamic property may especially facilitate falling asleep during periods when one is awake but desires to fall asleep or should fall asleep (including (undesired) nocturnal awakening). Hence, these dynamic effects are offered during a third predetermined period. The phrase "provide during a further predetermined period the first lighting element" and similar phrases may especially refer to the above indicated third predetermined period.

Hence, in a further aspect the invention also provides a lighting system comprising a first lighting element and a control unit for controlling the first lighting element to provide a first lighting element light, wherein the lighting system is configured to (a) adapt during a (first and/or second) predetermined period the first lighting element light to a general lighting level, and (b) adapt during a (third or further) predetermined period the first lighting element light to comprises a dynamic property selected from the group of moving or changing a light pattern, changing a color, and changing an intensity of said first lighting element light, even more especially to adapt during a (third or further) predetermined period the first lighting element light to a dimmed lighting level wherein the dimmed lighting level further comprises a dynamic property selected from the group of moving or changing a light pattern, changing a color, and changing an intensity of said first lighting element light.

It is especially desired that the dynamics are not too slow (then they are not perceived) but also not too fast. Especially, any change in the optical properties of the first lighting element light selected from moving the light pattern, a color change and an intensity change is especially gradual. Hence, especially, the control unit is configured to control a change in luminous flux at the light exit window at a specific wavelength is especially in the range of 0.1-5%/s, such as 0.5-4%/s. Alternatively or additionally, the control unit is (also) configured to control a change in intensity at a predetermined wavelength of the first lighting element light at any point in a plane of 1 $m^2$ perpendicular to a beam of light of first lighting element light at a second distance ($d2$) from the lighting element, with the second distance $0<d2\leq15$ m said first position in the range of 0.1-5%/s, such as 0.5-4%/s, especially with $0.5\leq d2\leq5$ m.

The third (or further) predetermined period can be a period that returns each day, and may be triggered by a time clock or digital time schedule, or by light conditions that are sensed by a sensor, such as above indicated third sensor. The third predetermined period can be triggered by a manual trigger. Hence, the control unit may include a (remote) user interface functionally coupled to said control unit. The third predetermined period may thus embodiments be a fixed period, such as 8 hours from 10 pm to 6 am, but may optionally also be a period that defined by a user. The third predetermined period may be the time between sunset and sunrise but the third predetermined period may also be the period that e.g. the general lighting illuminance level is below 50 lux (or another threshold value). In an embodiment, the functionality under d) is a default setting and the predetermined period is (thus) 24 hours. This may imply that always when the general lighting illuminance level is below the first threshold level, the first lighting element is switched on.

Especially, during the third (or further) period especially a plurality of times one or more of the following sequentially takes place (i) a move of a light pattern, (ii) a change of a light pattern), (iii) a color change of the light, and (iv) an intensity change of the light. Hence, for instance a sky with stars may be projected on a ceiling, wherein the a plurality of stars move (sequentially) over the ceiling. Or, for instance the color of the light may change from yellow to red an vice versa a plurality of times, etc. etc. Especially, those moves and/or changes occur gradually. Those moves and/or changes may according a predetermined sequence or random. Also a combination is possible, such as a random order of a plurality of predetermined sequences.

In embodiments, the (first) predetermined period and third (or further) predetermined period may be defined as a single predetermined period. In embodiments, the second predetermined period and third predetermined period may be defined as a single predetermined period. In embodiments, the first predetermined period, the second predetermined period and third predetermined period may be defined as a single predetermined period. Hence, in a specific embodiment the first predetermined period, the second predetermined period and the third predetermined period coincide.

In yet a further embodiment, wherein the first predetermined period, the second predetermined period and the third predetermined period start at a time selected from one or more ranges of 12 am-3 pm and 7 pm-11 pm. In another further embodiment, the lighting system further comprises a second sensor configured to sense nocturnal activity of a human, and wherein the control unit is configured to start providing first lighting element light with the dynamic property when nocturnal activity is above a predetermined nocturnal activity threshold value. Such sensor may e.g. include a motion sensor. It may also include a sensor that evaluates the type and/or depths of sleeping.

During the period that dynamic light effects are created, in embodiments also (dim) light may be provided that has a constant intensity. Hence, the lighting system, such as in an embodiment especially the lighting element, may be configured to provide during at least part of the (third) predetermined period first lighting element light with a dynamic property and second lighting element light having a static property (i.e. especially having constant intensity; even more especially color, color temperature and intensity are kept constant). In a further embodiment, to obtain these effects the lighting system may include a second lighting element (configured to provide second lighting element light).

As already indicated above, there is a relation between the luminous flux and the illuminance. The illuminances identified herein are especially relevant for the herein used first position (p1). This first position may especially be close to a bed, such as close to a pillow on a bed. Hence, the lighting system (and method; see below) may optionally be defined in terms of luminous fluxes.

Hence, in yet a further aspect, the invention also provides a lighting system comprising a first lighting element, an optional second lighting element, an optional first sensor, and a control unit, wherein: a) the first lighting element is configured to provide first lighting element light with controllable first lighting element luminous flux, wherein the lighting element luminous flux can be selected from a plurality of values in the range of 0-Φ, with Φ being a predetermined first lighting element maximum luminous flux, wherein the first lighting element maximum luminous flux is especially 10,000 Lumen, even more especially especially 5,000 Lumen; wherein the optional second lighting element is configured to provide second lighting element light with (optionally controllable) second lighting element luminous flux, and wherein especially the optional second lighting element has a maximum luminous flux of 100,000 Lumen; and wherein optionally the control unit and said optional first sensor are configured to evaluate a general lighting luminous flux; b) the control unit is especially configured to maintain a first lighting element luminous flux of the first lighting element, during a first predetermined period at a luminous flux value larger than zero when a (the) general lighting luminous flux level is below a predetermined first luminous flux threshold level, with the predetermined first luminous flux threshold level especially being 5,000 Lumen, especially being 500 Lumen, even more especially being 100 Lumen, such as 50 Lumen; c) the control unit is further especially configured to maintain the first lighting element luminous flux during a second predetermined period at a luminous flux value a*y*Φ when the general lighting luminous flux is y*Φ, y being the factor the general lighting luminous flux is below Φ, with 0<y<1, the parameter a being a predetermined lighting setting with 0<a≤1/y, (and with Φ being the predetermined first lighting element maximum luminous flux); and d) the lighting system is further especially configured to provide during a third predetermined period first lighting element light with a dynamic property especially selected from the group of a moving or changing light pattern, a color change, and an intensity change, wherein during the third period especially a plurality of times one or more of the following sequentially takes place (i) a move of a light pattern, (ii) a change of a light pattern), (iii) a color change of the light, and (iv) an intensity change of the light.

Hence, in yet a further aspect, the invention also provides a lighting system comprising a first lighting element and a control unit, wherein: a) the first lighting element is configured to provide first lighting element light with controllable lighting intensity, wherein the first lighting intensity can be selected from a plurality of values in the range of 0-I, with I being a predetermined first lighting element maximum intensity; b) the control unit is configured to maintain a first lighting element intensity during a first predetermined period at an intensity value larger than zero when a general lighting intensity is below a predetermined first threshold level; c) the control unit is further configured to maintain the first lighting element intensity during a second predetermined period at an intensity value a*y*I when the general lighting intensity level is y*I, y being the factor the general lighting intensity is below I, with 0<y<1, the parameter a being a predetermined lighting setting with 0<a≤1/y, (and with I being a predetermined first lighting element maximum intensity, see also above); and d) the lighting system is further configured to provide during a third predetermined period first lighting element light with a dynamic property selected from the group of a moving or changing light pattern, a color change, and an intensity change, wherein during the third period a plurality of times one or more of the following sequentially takes place (i) a move of a light pattern, (ii) a change of a light pattern), (iii) a color change of the light, and (iv) an intensity change of the light. For I for instance the luminous flux or the illuminance may be chosen.

Functionality (b) is especially relevant when the general lighting intensity is substantially zero, such as ≤⅕ of the predetermined first lighting element maximum intensity (which may optionally also be defined as predetermined first lighting element maximum illuminance or predetermined first lighting element maximum luminous flux), or when this intensity is zero (such as all artificial light sources switched off (except for the first lighting element). Functionality (c) is especially relevant when general lighting intensity is not zero, but relatively low, i.e. especially when the general lighting intensity is equal to or lower than the predetermined first lighting element maximum intensity. Again, these intensities may optionally be defined as illuminances or luminous fluxes.

Hence, for instance when the threshold value is 10 lux or 100 lumen (see above), the first lighting element may be switched on when the general illuminance or luminous flux, respectively, is below said threshold value, during a predetermined first period, which may optionally be dependent upon on the general illuminance or luminous flux, respectively. For instance, at the same time, dynamics may be provided to the light for a predetermined third period. When for instance the general illuminance or luminous flux, respectively, is between 10-50 lux, or between 100-5,000 lumen, respectively, the first lighting element may also be switched on (during the second predetermined period), and optionally scale the illuminance or luminous flux, respectively, of the first lighting element. During this period, or during part of this period, also dynamics may be provided to the light (for a predetermined third period).

As indicated above, in yet a further aspect, the invention also provides a method for controlling lighting in a room using a lighting system, especially as defined herein, the lighting system comprising a lighting element and a control unit, wherein the lighting element is configured to provide first lighting element light with controllable intensity, especially with controllable lighting element luminous flux, wherein the controllable intensity, especially the (controllable) lighting element luminous flux can be selected from a plurality of values in the range of 0-Φ, with Φ being a predetermined first lighting element maximum luminous flux, the method comprising:

maintaining the first lighting element illuminance at said first position (p1) especially at a first position (p1) within a first distance (d1) from the lighting element, with the first distance is especially 0<d1≤15 m, during a first predetermined period at a specific (variable) intensity, especially at an illuminance value larger than zero when a general lighting illuminance level at said first position (p1) is below a predetermined first threshold level;

maintaining the first lighting element illuminance at said first position (p1) during a second predetermined period especially at an illuminance value a*y*E when the general lighting illuminance level at said first position (p1) is y*E, y being the factor the general lighting illuminance is below E, with 0<y<1, a especially being a predetermined lighting setting with 0<a≤1/y, and with E being the predetermined first lighting element maximum illuminance at said first position (p1); and providing during a third predetermined period in a specific embodiment first lighting element light with a dynamic property, especially selected from the group of a moving or a changing of a light pattern, a color change, and an intensity change, wherein especially during the third period a plurality of times one or more of the following sequentially takes place (i) the moving of the light pattern, (ii) the changing of the light pattern), (iii) the color change of the embodiment first lighting element light, and (iv) the intensity change of the embodiment first lighting element light.

In yet a (more general) aspect, the invention provides also a method for controlling lighting in a room using a lighting system comprising a lighting element and a control unit, the method comprising adapting during a predetermined period first lighting element light of the first lighting element to a general lighting level, and providing during a predetermined period first lighting element light with a dynamic property selected from the group of a moving or a changing of a light pattern, a color change, and an intensity change, wherein during said period a plurality of times one or more of the following sequentially takes place (i) the moving of the light pattern, (ii) the changing of the light pattern), (iii) the color change of the first lighting element light, and (iv) the intensity change of the first lighting element light.

In a specific embodiment (of said method), said first position (p1) is within 1 meter from a bed, and wherein the method comprises starting the first predetermined period, the second predetermined period and the third predetermined period at a time selected from the range 7 pm-11 pm.

As indicated above, the system and/or method may be used to facilitate after nocturnal activity to fall asleep. Hence, the method may also include providing first lighting element light with the dynamic property when nocturnal activity is above a predetermined nocturnal activity threshold value. As too fast or to slow changes in the dynamics are not desired, the method may further comprise controlling a change in intensity at a predetermined wavelength of the first lighting element light at said first position in the range of 0.1-5%/s.

As indicated above, the lighting system may further comprise a second lighting element configured to provide second lighting element light. Hence, the method may further include controlling the intensity of the first lighting element light in relation to the intensity of the second lighting element light.

As already indicated above, there is a relation between the luminous flux and the illuminance. Hence, also the method may be defined in terms of luminous fluxes. Hence, in a further aspect the invention also provides a method for controlling lighting in a room using a lighting system, especially as defined in any one of the preceding claims, the lighting system comprising a lighting element, an optional first sensor, and a control unit, wherein (a) the lighting element is configured to provide first lighting element light with controllable first lighting element luminous flux, wherein the lighting element luminous flux can be selected from a plurality of values in the range of 0-$\Phi$, with $\Phi$ being a predetermined first lighting element maximum luminous flux, wherein the first lighting element maximum luminous flux is especially 10,000 Lumen, even more especially especially 5,000 Lumen, wherein the optional second lighting element is configured to provide second lighting element light with (optionally controllable) second lighting element luminous flux, and wherein especially the optional second lighting element has a maximum luminous flux of 100,000 Lumen; and wherein optionally the control unit and said optional first sensor are configured to evaluate a general lighting luminous flux; the method comprising: (b) maintaining a first lighting element luminous flux during a first predetermined period at an luminous flux value larger than zero when a general lighting luminous flux level is below a predetermined first luminous flux threshold level; (c) maintaining the first lighting element luminous flux during a second predetermined period at an illuminance value $a*y*\Phi$ when the general lighting luminous flux level at said first position (p1) is $y*\Phi$, y being the factor the general lighting luminous flux is below $\Phi$, with $0<y<1$, parameter a being a predetermined lighting setting with $0<a\leq1/y$; and (d) providing during a third predetermined period first lighting element light with a dynamic property selected from the group of a moving or changing light pattern, a color change, and an intensity change, wherein during the third period a plurality of times one or more of the following sequentially takes place (i) a move of a light pattern, (ii) a change of a light pattern), (iii) a color change of the light, and (iv) an intensity change of the light.

The invention further provides a computer program product, when run a computer configured to control a lighting system, especially as defined herein, according to the method as defined herein. Hence, the invention also provides a computer program product, when when running on a computer, is configured to perform the herein described method, especially control a lighting system according to such method.

Herein, the term "light intensity" may refer to one or more of luminous intensity and illuminance. Further, the phrase "included in the system" and similar phrases indicate that the described item is functionally coupled to the system.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like (such as "further" in "further predetermined period") in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

A computer program may be stored/distributed on a suitable non-transitory storage medium, such as an optical storage medium or a solid-state medium supplied together with or as part of other hardware, but may also be distributed in other forms, such as via the Internet or other wired or wireless telecommunication systems.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1:
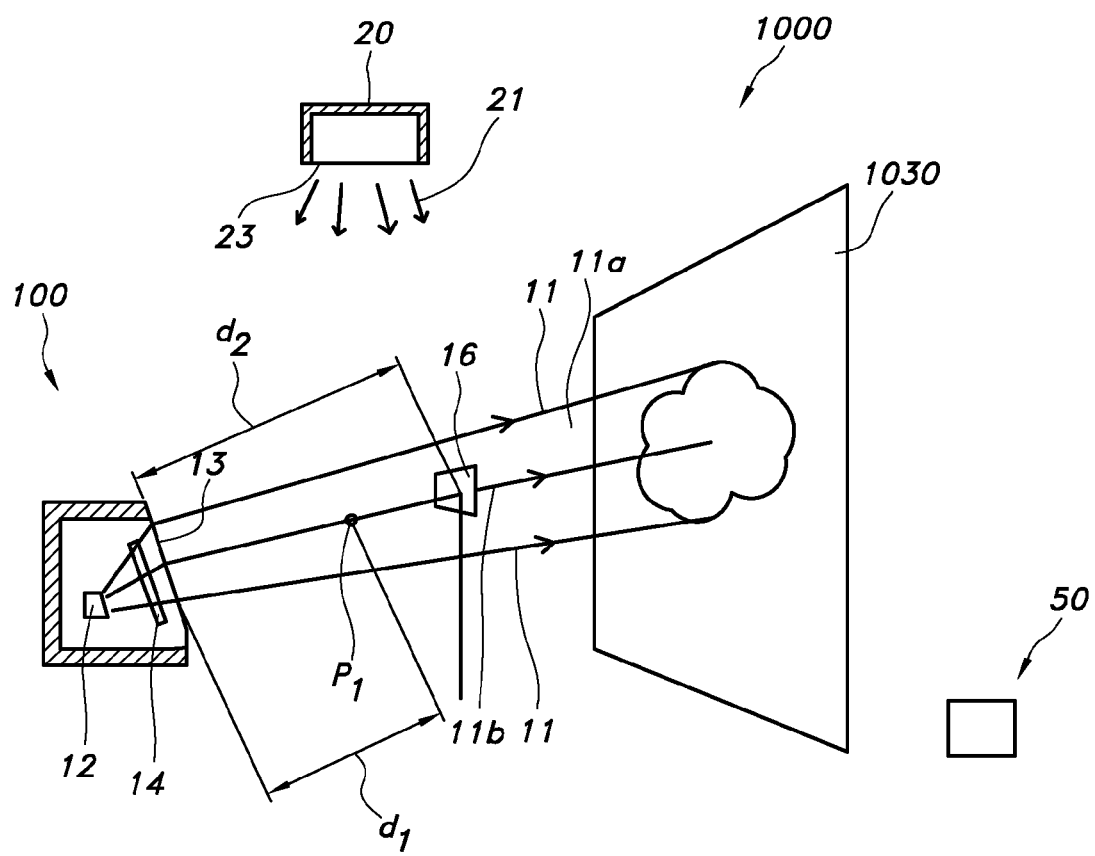
FIG. 1 schematically depicts an application of the system.

FIG. 1 schematically depicts a lighting system 100 comprising a first lighting element 10 and a control unit 50. The first lighting element 10 is configured to provide first lighting element light 11 with controllable first lighting element illuminance. A first position p1 is indicated, at which the illuminance may be evaluated. This first position p1 is within a first distance d1 from the lighting element 10, with the first distance 0<d1≤15 m.

The first lighting element has a light exit window 13. Further, the lighting system may be further configured to provide first lighting element light (11) with a dynamic property selected from the group of a moving or changing light pattern, a color change, and an intensity change. To this end, the lighting element may comprise a plurality of light sources, with reference indicated one or more light sources, and/or a display element, such as a moving element with a transparent (colored) piece or an LCD element. Other options are also possible to display colors or light patters on a wall and/or ceiling or other element which receives light 11 from the first lighting element. Reference 1030 indicates e.g. a wall in a room 1000.

Reference 20 indicates an optional second lighting element, also having a light exit window, indicated with reference 23. The $2^{nd}$ lighting element is configured to provide second lighting element light 21. The control unit 50 may be configured to control also such optional $2^{nd}$ lighting element 20.

Figure 2A:
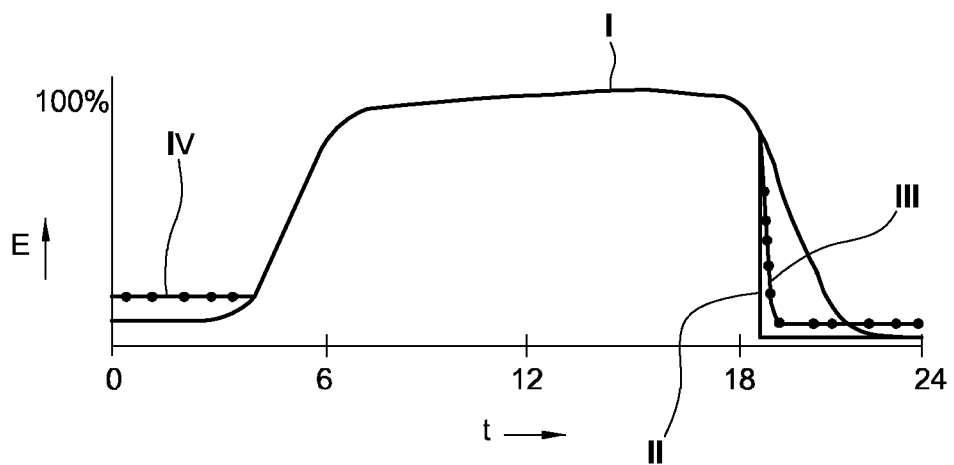
FIGS. 2a-2d schematically depict some aspects of the invention.
Figure 2B:
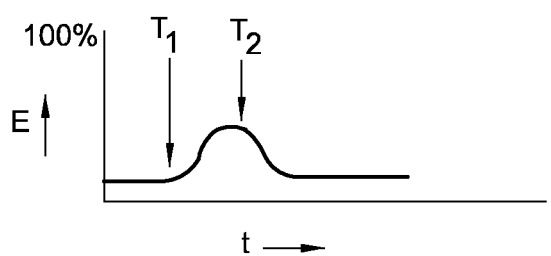
Figure 2C:
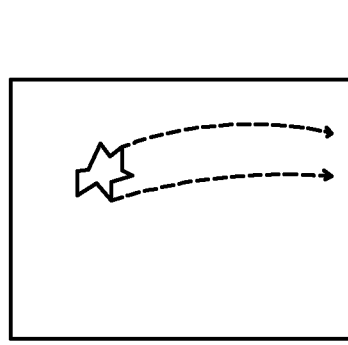
Figure 2D:
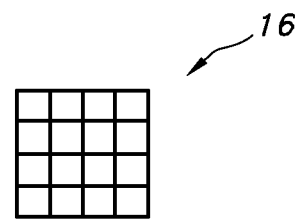

Reference 16 indicates a virtual plane at a distance d2 from the first lighting element 10, perpendicular to a ray 11b of beam 11a (see further also FIG. 2d).

Instead of a projection on a wall 1030, the first lighting element 100 may also project on the ceiling (not shown). Alternatively or additionally, a first lighting element may be provided as lighting element comprised by the ceiling. Hence, a pattern on a light exit window may be perceived by a person below the first lighting element (not shown).

FIG. 2a very schematically shows with curve I a possible progress of general lighting over a period of 24 hours, which may also includes a contribution of a second lighting element (or other source of non-natural light). Curve II indicates the deviation of such curve when suddenly the second lighting element is switched off and/or when e.g. blindings are closed. Curve III shows how the lighting system may compensate a too fast change in the general lighting illuminance. In this way, the first lighting element light arrives after some time at a level, especially higher than a background level, still perceivable by a person. Such level may be maintained during the night, see curve IV.

FIG. 2b schematically depicts an embodiment when e.g. a sensor senses nocturnal activity at time T1. At such moment, the first lighting element light (and also optionally light of the second lighten element, when available) may be increased to a certain amount, but to "normal" levels as during the day (indicated with 100%). When at T2 the sensor perceives that the person starts to fall asleep again and/or enters a bed, the level may decrease again.

FIG. 2c very schematically depicts a dynamical effect, such as a moving (and optionally fading) star on a wall 1030. Of course, all kind of dynamic effects are possible. Further, note that the first lighting element may be used in a projection mode and/or in a direct mode. For instance, the first lighting element may also be a light tile on a wall or ceiling which may be perceived directly. Hence, in an embodiment FIG. 2c may also schematically depict a ceiling or a part of a ceiling with a first lighting element (in operation).

FIG. 2d schematically depicts virtual plane 16. This plane is used to define in a way the minimum and maximum change in intensity. At each point in the plane, the intensity at a specific wavelength should preferably change in a range of 01.-5%/s. Referring to FIG. 1, the control unit 50 is configured to control a change in intensity at a predetermined wavelength of the first lighting element light 11 at any point in a plane 16 of 1 m² perpendicular to a beam of light 11 of first lighting element light 11 at a second distance d2 from the lighting element 10, with the second distance 0<d2≤15 m said first position in the range of 0.1-5%/s.

Figure 3:
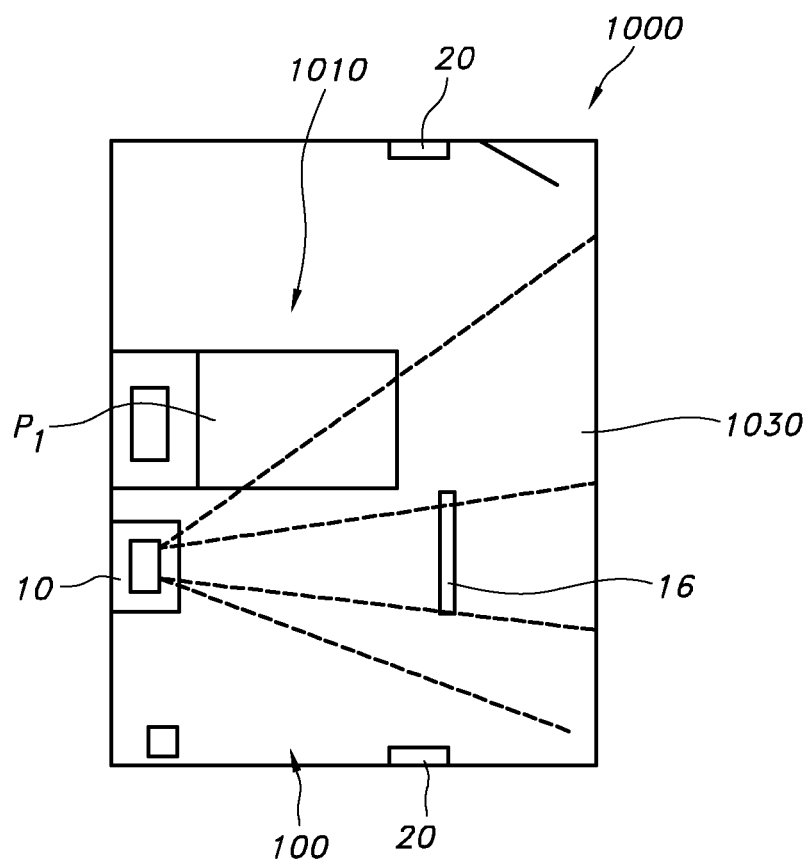
FIG. 3 schematically depicts an application of the system.
The drawings are not necessarily on scale.

FIG. 3 schematically depicts a further application, e.g. in a bedroom or hospital room 1000.

The illuminance levels of the dynamic dim light effect are especially low, preferably less than 30 lux, or even better <10 lux. This facilitates a rapid sleep onset (no melatonin suppression), but also allows for a gradual wake up. Moreover during nocturnal awakenings the dynamic dim light effect will help to ease returning to sleep and reduce nocturnal restlessness.

In order to facilitate unwinding and relaxation some, or all, of the (il)luminated areas of the dim light effect are dynamic in nature. The dynamics can be in the (1) intensity of the dim light effect that is gradually changing, for instance producing light intensity changes that mimic a glowing fireplace; (2) changing spectral composition: for instance moving from orange to red to yellow with some pattern over time, or a color change along the blackbody line, optionally in combination with 1; (3) changing the location of the illuminated areas: (a) Gradually: like when projecting through a rotating slide with some patterns/figures on it. (b) abruptly: for instance by a large area pixelated light source; and (4) any combination of two or three of (1)-(3).

The preferred dynamics has in an embodiment a cycle time of 1 to 120 seconds, preferably 2-10 seconds if the dynamics is a glowing effect. However, larger cycle times are also possible (see above). Further, as indicated above, a random generation of the dynamics is also possible In an embodiment, projection can be used to generate a dynamic dim light effect. Alternatively, different types of light patterns can be created with a ceiling containing a pixilated distribution of LED point sources. In general, glowing light effects are created with sinusoidal variation of light output. Preferably, the dynamic dim light effects are offered in the bedtime period, either during the full bed period, or only while falling asleep and/or waking up. The dim light dynamic effects during the bedtime period need not remain identical. Different effects can be used during different parts of the bedtime period: (A) while falling asleep (f.i. using yellow or red light effects, to unwind with light effects that do not suppress the sleep promoting hormone melatonin); (B) while maintaining sleep (f.i. a starry sky appearance with LEDs placed over the ceiling area); (C) while waking up (f.i. adding a rising sun effect by means of a wall washer to the starry sky, gradually enhancing both brightness and the blue light content, to wake people up more effectively). Another option can be to create a bright light condition in the morning with on/off dynamics that result in flicker/flashes that act as an alarm clock to wake people more efficiently/rapidly after a night's sleep.

The system can be connected to the biofeedback signals from a camera, Actiwatch, IPhone sleep App, motion sensors, sound. Upon detection of a biofeedback signal above a threshold, and a time signal one of the above light effects is created.

In an embodiment, general lighting created with a pixilated ceiling luminaire, preferably embodied in ceiling tiles, covering the whole ceiling in the area where beds are present, can be provided.

In another embodiment, at first the "starry sky" simulation can be used: the individual LED points glow in random order. Here, glowing may mean that the light output varies between two levels of light output, in a cyclic manner, possibly with a color temperature change as well (more reddish light (low color temperature) at minimum light level) and more bluish light (high color temperature) at high maximum light output). "Random order" may mean that the phases of the dimming cycle for the different light points are different according a random distribution. To obtain the warm dimming behavior a red LED is mixed with cool white LEDs. To obtain the starry sky effect, the light output of each LED point is in a different phase of the cyclic repetition of the glowing behavior. To make the starry sky even more realistic, some LED points have a higher light level compared with other, in this way for instance the "Great Bear" sign can be simulated. These signs can be changed depending on the time of the year, thus the light effect is coupled to a year-clock. In a further embodiment, the use of tunable parameters may be important to provide customization of the light effect to individual user needs: (a) the difference in light output between the minimum and maximum light level as well as the minimum light level can be fine tuned by the user via the user interface; and/or (b) the speed of the dynamic light change (=dimming cycle time) can be fine tuned by the user via the user interface. Since the intention is to have a relaxing nocturnal light effect, moderate to slow speed of the cyclic behavior is required (one cycle with variable dimming per light point takes at least 2 seconds or more).

In another embodiment, artistic dynamic patterns (e.g. moving waves or water rippling) can be used, that can be set to a glowing mode as well. Again, the difference in light output between the minimum and maximum light level, the minimum light level and the speed of the dynamic light change can be fine tuned by the user via the user interface.

In the morning, the ceiling creates bright light just before wakeup time (the wake-up light effect). With presence detection above the beds, light can be switched on in local areas only, in case more than one bed is present in the same space.

Application may e.g. in Neonatal Intensive Care Units, bedrooms in care facilities for demented elderly, in hospital patient rooms on pediatric or geriatric wards, in hotels, in baby bedrooms, in bedroom lighting systems for homes, etc.

The invention claimed is:
1. A lighting system comprising a first lighting element and a control unit for controlling the first lighting element to provide a first lighting element light, wherein the lighting system is configured to:
provide during a predetermined period the first lighting element light to a first lighting level, and
provide during a further predetermined period the first lighting element light to a second or dimmed light level or condition wherein the dimmed light condition further comprises a dynamic property selected from the group of moving or changing a light pattern, changing a color, and cyclic varying an intensity of said first lighting element light,
the first lighting element is configured to provide first lighting element light with a controllable lighting element luminous flux, wherein the lighting element luminous flux is being selected from a plurality of values in the range of $0\text{-}\phi$, with $\phi$ being a predetermined first lighting element maximum luminous flux;
the control unit is configured to maintain a first lighting element illuminance at a first position (p1) within a first distance (d1) from the lighting element, with the first distance $0 < d1 \leq 15$ m, during a first predetermined period at an illuminance value larger than zero when a general lighting illuminance level at said first position (p1) is below a predetermined first threshold level;
the control unit is further configured to maintain the first lighting element illuminance at said first position (p1) during a second predetermined period at an illuminance value $a*y*E$ when the general lighting illuminance level at said first position (p1) is $y*E$, y being the factor the general lighting illuminance is below E, with $0 < y < 1$, the parameter being a predetermined lighting setting with $0 < a \leq 1/y$, and with E being a predetermined first lighting element maximum illuminance at said first position (p1); and
the lighting system is further configured to provide during a third predetermined period first lighting element light with said dynamic property selected from the group of a moving or a changing of a light pattern, a color change, and an intensity change, wherein during the third period a plurality of times one or more of the following sequentially takes place (i) the moving of the light pattern, (ii) the changing of the light pattern), (iii) the color change of the first lighting element light, and (iv) the intensity change of the first lighting element light.

2. The lighting system according to claim 1, wherein the predetermined first threshold level of the general lighting illuminance is 50 lux or smaller, wherein the predetermined first lighting element maximum illuminance is 50 lux, and wherein the first lighting element has a predetermined first lighting element maximum luminous flux ($\phi$) of 5,000 Lumen.

3. The lighting system according to claim 1, further comprising a second lighting element configured to provide second lighting element light, wherein the general lighting illuminance is defined as the illuminance at said first position (p1) provided by said second lighting element light, wherein the first lighting element has a maximum luminous flux of 5,000 Lumen and wherein the second lighting element has maximum luminous flux of 100,000 Lumen.

4. The lighting system according to claim 1, wherein the general lighting illuminance is defined as the illuminance at said first position (p1) provided by light of any lighting element except for said first lighting element light, wherein the lighting system further comprises a first sensor, and wherein the control unit and said first sensor are configured to evaluate the general lighting illuminance at said first position (p1).

5. The lighting system according to claim 1, wherein the control unit is configured to control the predetermined lighting setting a to a value n, when $y \le 1/n$, with n=2, and wherein the first predetermined period, the second predetermined period and the third predetermined period coincide.

6. The lighting system according to claim 1, wherein the control unit is configured to gradually decrease the first lighting element illuminance from a first value to a second value.

7. The lighting system according to claim 1, wherein the control unit is configured to control a change in intensity at a predetermined wavelength of the first lighting element light at any point in a plane of 1 m$^2$ perpendicular to a beam of light of first lighting element light at a second distance (d2) from the lighting element, with the second distance $0<d2\le15$ m said first position in the range of 0.1-5%/s.

8. The lighting system according to claim 1, wherein the first predetermined period, the second predetermined period and the third predetermined period start at a time selected from one or more ranges of 12 am-3 pm and 7 pm-11 pm, the lighting system further comprising a second sensor configured to sense nocturnal activity of a human, and wherein the control unit is configured to start providing first lighting element light with the dynamic property when nocutural activity is above a predetermined nocturnal activity threshold value.

9. A method for controlling lighting in a room using a lighting system comprising a lighting element and a control unit, wherein the lighting element is configured to provide first lighting element light with controllable first lighting element luminous flux, wherein the lighting element luminous flux is being selected from a plurality of values in the range of 0-$\phi$, with $\phi$ being a predetermined lighting element maximum luminous flux, the method comprising:
providing during a predetermined period first lighting element light of the first lighting element (10) to a first lighting level,
providing during a further predetermined period first lighting element light to a second or dimmed light level or condition wherein the dimmed light condition further comprising a dynamic property selected from the group of a moving or changing of a light pattern, changing a color change, and cyclic varying an intensity,
maintaining a first lighting element illuminance at said first position (p1) within a first distance (d1) from the lighting element, with the first distance $0<d1\le15$ m during a first predetermined period at an illuminance value larger than zero when a general lighting illuminance level at said first position (p1) is below a predetermined first threshold level;
maintaining the first lighting element illuminance at said first position (p1) during a second predetermined period at an illuminance value a*y*E when the general lighting illuminance level at said first position (p1) is y*E, y being the factor the general lighting illuminance is below E, with $0<y<1$, the parameter a being a predetermined lighting setting with $0<a\le1/y$, and with E being a predetermined first lighting element maximum illuminance at said first position (p1); and
providing during a third predetermined period first lighting element light with a dynamic property selected from the group of a moving or a changing of a light pattern, a color change, and an intensity change, wherein during the third period a plurality of times one or more of the following sequentially takes place (i) the moving of the light pattern, (ii) the changing of the light pattern), (iii) the color change of the first lighting element light, and (iv) the intensity change of the first lighting element light.

10. The method according to claim 9, wherein said first position (p1) is within 1 meter from a bed, and wherein the method comprises starting the first predetermined period, the second predetermined period and the third predetermined period at a time selected from the range 7 pm-11 pm, the method further comprising providing first lighting element light (11) with the dynamic property when nocutural activity is above a predetermined noctural activity threshold value.

11. The method according to claim 9, comprising controlling a change in intensity at a predetermined wavelength of the first lighting element light at said first position in the range of 0.1-5%/s, and wherein the predetermined first threshold level of the general lighting illuminance is 50 lux and wherein the first lighting element has a maximum luminous flux of 5,000 Lumen.

12. The method according to claim 9, wherein the lighting system further comprises a second lighting element configured to provide second lighting element light, wherein the intensity of the first lighting element light is controlled in relation to the intensity of the second lighting element light, wherein the first lighting element has a predetermined first lighting element maximum luminous flux of 5,000 Lumen and wherein the second lighting element has maximum luminous flux of 100,000 Lumen.

13. A computer program product, when run a computer configured to control a lighting system according to the method of claim 9.

* * * * *